US011202701B2

(12) United States Patent
Leuthardt et al.

(10) Patent No.: US 11,202,701 B2
(45) Date of Patent: Dec. 21, 2021

(54) DEVICE AND METHOD OF INHIBITING ENDOLEAKS

(71) Applicant: Washington University, St. Louis, MO (US)

(72) Inventors: Eric C. Leuthardt, St. Louis, MO (US); Greg Zipfel, St. Louis, MO (US); Colin Derdeyn, St. Louis, MO (US); Chandu Vemuri, St. Louis, MO (US); Philip V. Bayly, St. Louis, MO (US); Guy Genin, St. Louis, MO (US); Katie McCoy, St. Louis, MO (US); Junwoo Suh, St. Louis, MO (US); Yuni Teh, St. Louis, MO (US); Alan Zhao, St. Louis, MO (US); Donald Elbert, St. Louis, MO (US)

(73) Assignee: Washington University, St. Louis, MO (US)

( * ) Notice: Subject to any disclaimer, the term of this patent is extended or adjusted under 35 U.S.C. 154(b) by 156 days.

(21) Appl. No.: 16/312,555

(22) PCT Filed: Jun. 30, 2017

(86) PCT No.: PCT/US2017/040292
§ 371 (c)(1),
(2) Date: Dec. 21, 2018

(87) PCT Pub. No.: WO2018/005969
PCT Pub. Date: Jan. 4, 2018

(65) Prior Publication Data
US 2019/0231513 A1    Aug. 1, 2019

Related U.S. Application Data

(60) Provisional application No. 62/364,945, filed on Jul. 21, 2016, provisional application No. 62/357,018, filed on Jun. 30, 2016.

(51) Int. Cl.
*A61F 2/07* (2013.01)
*A61F 2/82* (2013.01)

(52) U.S. Cl.
CPC .................. *A61F 2/07* (2013.01); *A61F 2/82* (2013.01); *A61F 2002/077* (2013.01); *A61F 2002/823* (2013.01)

(58) Field of Classification Search
CPC ........ A61F 2/07; A61F 2/82; A61F 2002/823; A61F 2002/077
See application file for complete search history.

(56) References Cited

U.S. PATENT DOCUMENTS 5,360,443 A * 11/1994 Barone ............. A61M 25/1002
623/1.13
5,366,504 A * 11/1994 Andersen .................. A61F 2/04
606/194

(Continued)

FOREIGN PATENT DOCUMENTS

EP          2777616 A1     9/2014
WO    2008051279 A1     5/2008

(Continued)

OTHER PUBLICATIONS

Buchanan, L. W. et al. "Endovascular Repair of Aortic Disease: A Venture Capital Perspective." Seminars in Interventional Radiology. Thieme Medical Publishers, 2009.

(Continued)

*Primary Examiner* — Julian W Woo
(74) *Attorney, Agent, or Firm* — Armstrong Teasdale LLP

(57) ABSTRACT

A stent for placement in a blood vessel with a wall having an aneurysm including an endovascular graft having a first end, a second end, and a tubular body that is expandable and extends from the first end to the second end. The stent also includes a coagulation apparatus attached to the tubular body between the first and second ends. The coagulation (Continued)

apparatus has a frame and a coagulant attached to the frame. When the stent is deployed within the blood vessel, the tubular body extends across the aneurysm and expands at the first and second ends to seal against the wall of the blood vessel such that blood is channeled across the aneurysm through the tubular body such that a pocket of blood is defined external to the tubular body. The frame expands into the pocket to orient the coagulant therein and promote coagulation of blood within the pocket.

19 Claims, 2 Drawing Sheets

(56) References Cited

U.S. PATENT DOCUMENTS

| | | | | |
|---|---|---|---|---|
| 5,665,117 | A | * | 9/1997 | Rhodes ..................... A61F 2/07 606/192 |
| 7,766,959 | B2 | * | 8/2010 | DiMatteo .................. A61F 2/06 623/1.16 |
| 8,277,499 | B2 | * | 10/2012 | Christiansen ............. A61F 2/07 623/1.13 |
| 8,641,777 | B2 | | 2/2014 | Strauss et al. |
| 8,771,294 | B2 | | 7/2014 | Sepetka et al. |
| 8,940,040 | B2 | * | 1/2015 | Shahriari ............... A61F 2/2418 623/1.35 |
| 8,945,199 | B2 | | 2/2015 | Ganpath et al. |
| 10,034,788 | B2 | * | 7/2018 | Kasprzak, II ........... A61F 2/962 |
| 10,188,500 | B2 | * | 1/2019 | Perkins ................. A61F 2/0077 |
| 2003/0236567 | A1 | | 12/2003 | Elliot |
| 2004/0167597 | A1 | | 8/2004 | Costantino et al. |
| 2005/0165467 | A1 | | 7/2005 | Hunter et al. |
| 2005/0165480 | A1 | | 7/2005 | Jordan et al. |
| 2011/0301696 | A1 | | 12/2011 | Mangiardi |
| 2012/0089218 | A1 | | 4/2012 | Dardi |
| 2013/0274873 | A1 | | 10/2013 | Delaloye et al. |
| 2014/0288633 | A1 | | 9/2014 | Burke et al. |
| 2015/0073523 | A1 | | 3/2015 | Chobotov |

FOREIGN PATENT DOCUMENTS

| | | |
|---|---|---|
| WO | 2014159746 A1 | 10/2014 |
| WO | 2015183489 A1 | 12/2015 |

OTHER PUBLICATIONS

Mousa, A. Y. et al. "Update on the Diagnosis and Management of Popliteal Aneurysm and Literature Review." Vascular 14.2 (2006): 103-08. Abstract.

Airaksinen, K. J. et al. "Drug-eluting Stents in Patients on Long-term Oral Anticoagulation Therapy: A Mission Impossible?" Interventional Cardiology 2.2 (2010): 127-35.

USFDA Summary of Safety and Effectiveness Data for GORE® VIABAHN® Endoprosthesis, GORE® VIABAHN® Endoprosthesis with Heparin BioActive Surface devices.

Nikolsky, E. et al. "Stent Deployment Failure: Reasons, Implications, and Short- and Long-term Outcomes." Cathet. Cardiovasc. Intervent. Catheterization and Cardiovascular Interventions 59.3 (2003): 324-28. Abstract.

International Search Report for International Application No. PCT/US2017/040292, dated Sep. 21, 2017, 2 pages.

Written Opinion of the International Searching Authority for International Application No. PCT/US2017/040292, dated Sep. 21, 2017, 4 pages.

* cited by examiner

DEVICE AND METHOD OF INHIBITING ENDOLEAKS

CROSS REFERENCE TO RELATED APPLICATION

This application is a U.S. National Phase Application of PCT/US2017/040292, filed Jun. 30, 2017, which claims the benefit of priority to U.S. Provisional Patent Application Ser. No. 62/357,018, filed Jun. 30, 2016 and entitled STENT, and U.S. Provisional Patent Application Ser. No. 62/364,945, filed Jul. 21, 2016 and entitled DEVICE AND METHOD OF INHIBITING ENDOLEAKS, the contents of which are hereby expressly incorporated by reference in their entirety.

BACKGROUND

The present disclosure relates generally to devices and, more particularly, to an intravascular stent for treating an endoleak in an aneurysm and methods of using such a stent.

In some instances, a weakened wall of a blood vessel may bulge (or become aneurysmal) in response to the pressure of blood flowing along the lumen of the vessel, such that a sack of blood develops on the vessel. One known method of treating some aneurysms (such as, for example, abdominal aortic aneurysms) is to perform an endovascular aneurysm repair (EVAR) procedure during which an endovascular graft is inserted into the lumen at the site of the aneurysm. The graft blocks the flow of blood from the lumen into the aneurysm sack in an effort to stop the continual pressure increase within the sack and, in turn, prevent the weakened wall from rupturing under the pressure.

In some instances, however, an endoleak may develop at the site of the aneurysm, such that blood flow into the sack persists even though the graft is functioning properly. For example, in the event of a Type II endoleak, blood may flow into the aneurysm sack from the smaller blood vessels attached to the weakened wall itself. This can cause the pressure within the sack (and, hence, the size of the sack) to continually increase despite the presence of a properly-functioning graft, which can ultimately cause the weakened wall to unexpectedly rupture under the pressure.

It is desirable, therefore, to provide an aneurysm-treatment device that inhibits and/or blocks blood flow from the lumen into the aneurysm sack, while also inhibiting and/or stopping endoleaks of blood into the sack.

SUMMARY

In one aspect, a stent for placement in a blood vessel with a wall having an aneurysm is provided. The stent includes an endovascular graft having a first end, a second end, and a tubular body that is expandable and extends from the first end to the second end. The stent also includes a coagulation apparatus attached to the tubular body of the endovascular graft between the first end and the second end. The coagulation apparatus has a frame and a coagulant attached to the frame. When the stent is deployed within the blood vessel, the tubular body extends across the aneurysm and is configured to expand at the first end and the second end to seal against the wall of the blood vessel such that blood is channeled across the aneurysm through the tubular body such that a pocket of blood is defined external to the tubular body. The frame is configured to expand into the pocket to orient the coagulant within the pocket and promote coagulation of the blood within the pocket.

In another aspect, a method of inhibiting endoleaks in a blood vessel with a wall having an aneurysm is provided. The method includes inserting a stent within the blood vessel at a site of the aneurysm. The stent includes an endovascular graft, having a tubular body, and a coagulation apparatus attached to the tubular body. The coagulation apparatus has a frame and a coagulant attached to the frame. The method further includes deploying the coagulation apparatus from a compressed state such that the frame expands into a pocket of blood, defined by the aneurysm, to orient the coagulant within the pocket and promote coagulation of the blood within the pocket.

DETAILED DESCRIPTION OF THE DRAWINGS

Figure 1:
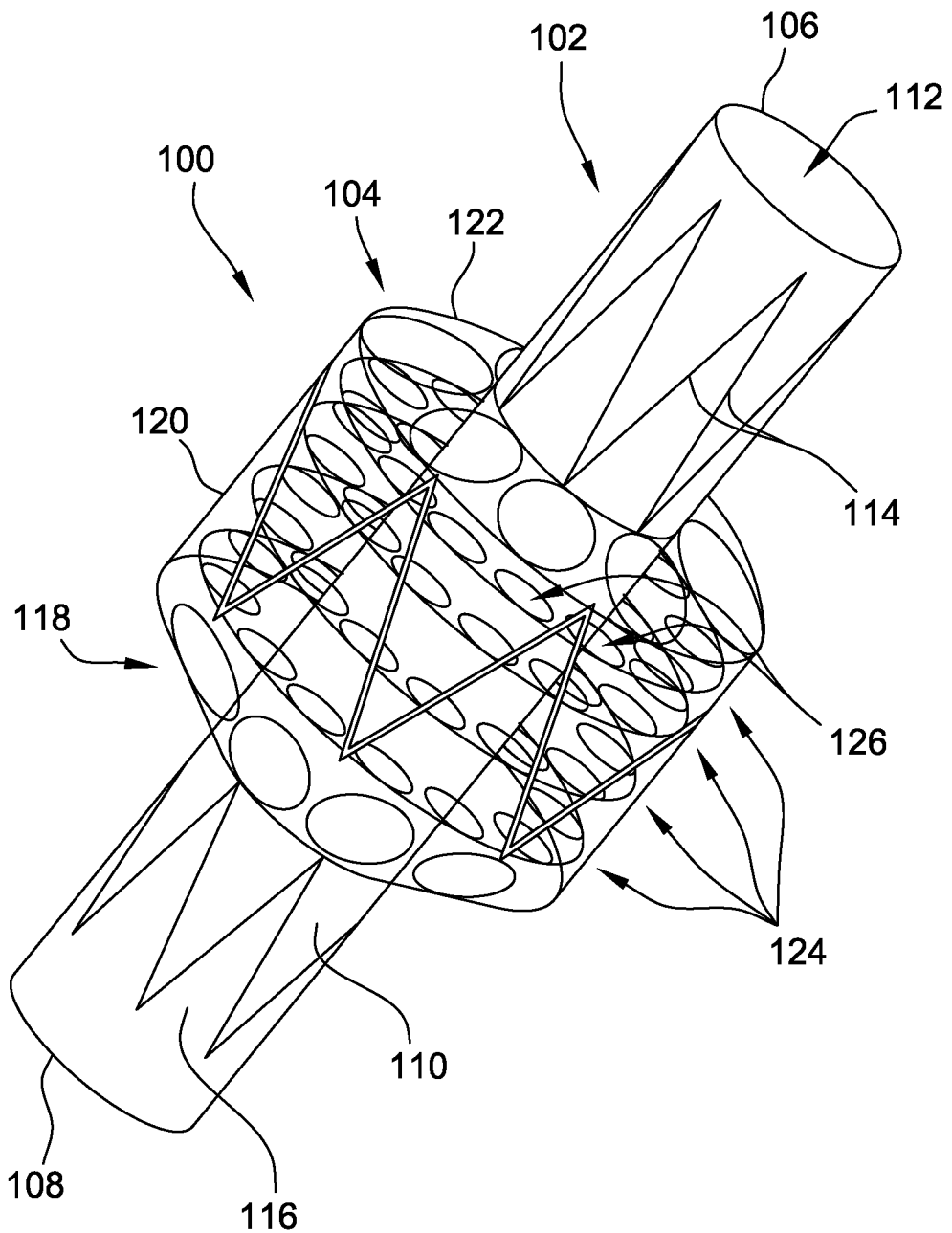
FIG. 1 is a perspective view of an embodiment of a stent.

FIG. 1 illustrates one suitable embodiment of a stent, indicated generally at 100. In the illustrated embodiment, the stent 100 has an endovascular graft 102 and a coagulation apparatus 104 attached to the graft 102. The graft 102 has a first end 106, a second end 108, and a tubular (e.g., substantially cylindrical) body 110 extending from the first end 106 to the second end 108 such that the body 110 defines a lumen 112 through the graft 102. The illustrated body 110 has an expandable cage 114 and a substantially liquid-impermeable cover 116 attached to the cage 114. Although the cage 114 is attached to the exterior of the cover 116 in the illustrated embodiment (i.e., the cage 114 is not positioned within the lumen 112), the cage 114 may be attached to the interior of the cover 116 in other embodiments (i.e., the cage 114 may be positioned within the lumen 112 in other embodiments).

In some embodiments, the cage 114 may be fabricated from a shape-memory material (e.g., a nitinol material), and the cover 116 may be fabricated from a fabric (e.g., a woven fabric) such that the cover 116 is sewn or bonded to the cage 114. In other embodiments, the body 110 may not have separate cage and cover structures, but, instead, the body 110 may be a single, unitary structure in the form of a liquid-impermeable, semi-rigid panel of molded, self-supporting, shape-memory material that is expandable and substantially liquid-impermeable. Alternatively, the body 110 may have any suitable number of structures that are fabricated from any suitable materials (e.g., the cage 114 may be fabricated from steel, titanium, plastic, etc.) and that are attached in any suitable manner using any suitable methods that enable the graft 102 to function as described herein.

The coagulation apparatus 114 includes a coagulant 118 and a frame 120 for orienting the coagulant 118 relative to the graft 102 upon deployment of the stent 100, as set forth in more detail below. In the illustrated embodiment, the frame 120 is a ring-shaped mechanism that circumscribes the graft 102, and the frame 120 is fabricated from a shape-memory material (e.g., a nitinol material) such that the frame 120 is radially expandable relative to the graft 102. In that regard, the coagulant 118 is in the form of a porous web 122 of thrombogenic material (e.g., a fibrous material such as silk strands (or sutures), nano-constructed fibers carrying collagen or tissue factor, etc.) by which the frame 120 is circumferentially tethered to the graft 102 so as to limit the radial expansion of the frame 120 relative to the graft 102. For example, in the illustrated embodiment, the web 122 has a plurality of overlapping tiers 124, each including at least one fibrous strand shaped or oriented to define a lattice-like network of pores 126. Although the frame 120 is attached to the graft 102 via the coagulant 118 in the illustrated embodiment, the coagulant 118 may alternatively be attached to the graft 102 via the frame 120 in other embodiments (e.g., a suitable frame may be soldered to the cage 114, with a suitable coagulant attached to the frame). Moreover, the frame 120 may be fabricated from any suitable material in other embodiments (e.g., steel, titanium, plastic, etc.).

Figure 2:
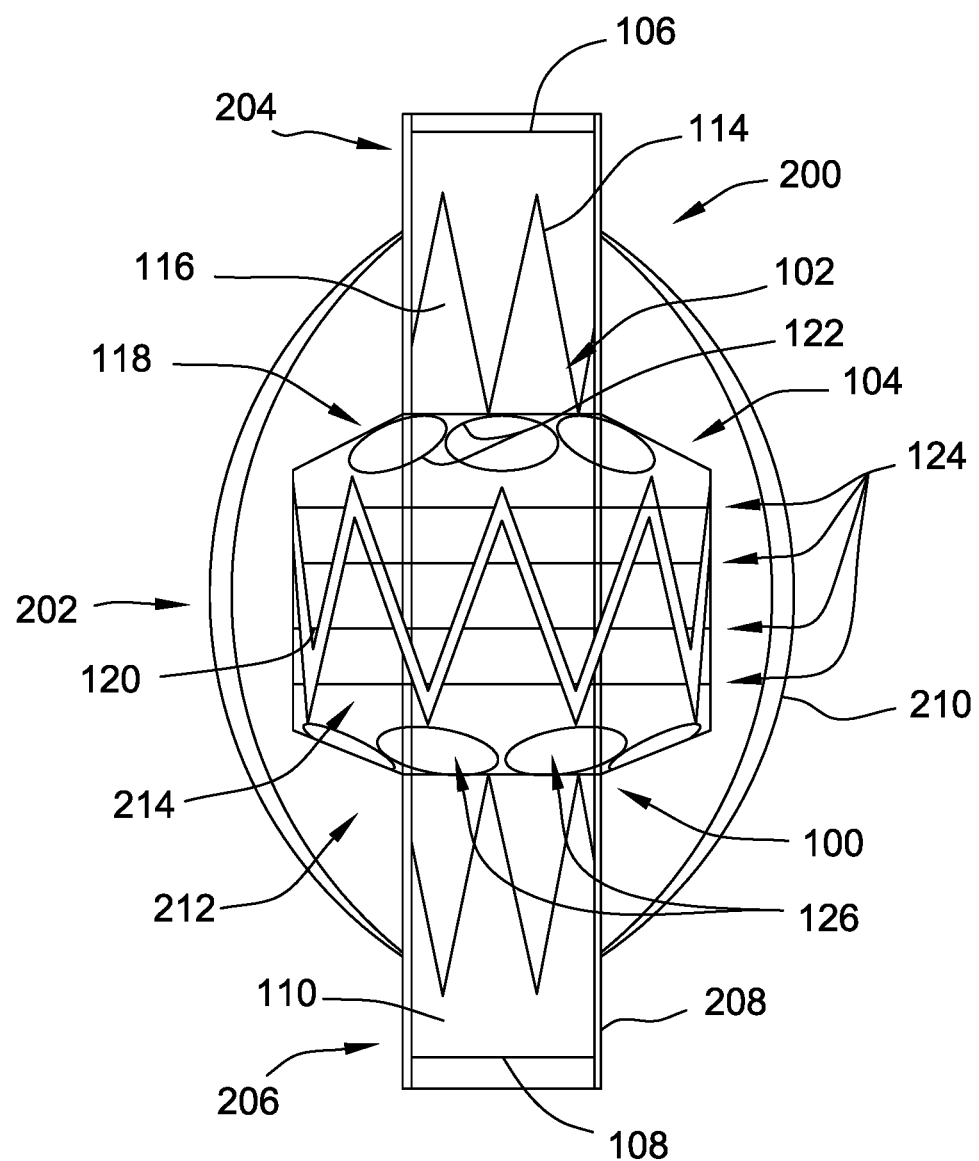
FIG. 2 is a schematic illustration of the stent shown in FIG. 1 deployed at the site of an aneurysm in a blood vessel.
Corresponding reference characters indicate corresponding parts throughout the several views of the drawings.

With reference now to FIG. 2, the stent 100 is designed for intravascular placement in a blood vessel 200 at the site of an aneurysm 202 (e.g., an aortic aneurysm, a popliteal aneurysm, or more broadly any extracranial large vessel fusiform aneurysm). To place the stent 100 within the vessel 200, the stent 100 is initially compressed within a sheath (not shown), such that the frame 120 of the coagulation apparatus 104 is seated against the cage 114 of the graft 102 with the web 122 at least in part sandwiched between the frame 120 and the body 110. The sheath is then inserted into the vessel 200 while the stent 100 is contained within the sheath, and the stent 100 is ultimately deployed from the sheath at the site of the aneurysm 202 such that the first end 106 of the graft 102 is positioned on a first side 204 of the aneurysm 202, the second end 108 of the graft 102 is positioned on a second side 206 of the aneurysm 202, and the coagulation apparatus 104 is aligned with the aneurysm 202.

When the stent 100 is deployed from the sheath, the cage 114 is permitted to at least partially decompress, and the cage 114 expands radially outward as a result. The first end 106 of the graft 102 seats firmly against the wall 208 of the vessel 200 on the first side 204 of the aneurysm 202, and the second end 108 of the graft 102 seats firmly against the wall 208 of the vessel 200 on the second side 206 of the aneurysm 202. The body 110 of the graft 102 thus channels blood across the aneurysm 202 in a manner that isolates a bulging segment 210 of the vessel wall 208 from the pressure of the blood flow, thereby defining an enclosed pocket 212 of blood between the bulging wall segment 210 and the body 110 of the graft 102. Because the graft 102 seals against the vessel wall 208 at the ends 106, 108, the graft 102 inhibits and/or prevents blood from flowing between the wall 208 and the graft 102 into the pocket 212. Moreover, because the body 110 of the graft 102 is substantially liquid-impermeable, the graft 102 also prevents blood flowing through the lumen 112 from entering the pocket 212 through the body 110.

Notably, the frame 120 of the coagulation apparatus 104 is also permitted to decompress (e.g., completely decompress) when the stent 100 is deployed from the sheath. More specifically, the frame 120 expands radially outward into the pocket 212 such that the frame 120 is radially spaced apart from the body 110 of the graft 102 about the entire circumference of the body 110. Thus, the web 122 tautly spans the space 214 defined between the frame 120 and the body 110 of the graft 102. In the illustrated embodiment, when the frame 120 is fully expanded, the frame 120 does not contact the bulging wall segment 210 within the pocket 212 but, rather, the frame 120 is spaced apart therefrom. In other embodiments, however, the frame 120 may be sized and/or shaped to seat against the bulging wall segment 210 within the pocket 212 when the frame expands into the pocket 212. Notably, although the cage 114 and the frame 120 are self-expandable in the illustrated embodiment, the cage 114 and/or the frame 120 may be deployed on a balloon-expandable platform in other embodiments.

Because the graft 102 inhibits and/or prevents blood from flowing into the pocket 212 as set forth above, the graft 102 also inhibits and/or prevents blood from evacuating the pocket 212, which effectively traps a somewhat stagnant quantity of blood within the pocket 212 after the stent 100 is deployed. In that regard, the porous nature of the web 122 permits blood to occupy the space 214 between the frame 120 and the body 110 of the graft 102 within the pocket 212 such that the blood within the space 214 contacts the coagulant 118, thereby initiating platelet adhesion and a blood coagulation cascade. The blood within the pocket 212 then starts to coagulate (or clot), creating a solid biological barrier which ensures that additional blood does not flow into the pocket 212 as the result of an endoleak (e.g., a Type II endoleak). Notably, the overlapping-tiers 124 and lattice-like nature of the web 122 provide for multiple simultaneous coagulation points inside the pocket 212, which promotes a more rapid and evenly distributed clotting response. Moreover, the coagulation of blood within the pocket 212 ultimately leads to homeostasis, thereby triggering the body's wound healing process and ultimately causing fibrosis of the resulting blood clot, which can serve to shrink the size of the aneurysm 202 over time. Notably, in addition to being self-expandable, the cage 114 and the frame 120 constructed as set forth above are likewise collapsible after having been deployed (such as, for example, when a predefined amount of force is applied thereto as a result of the blood clot starting to fibrose, scar, and contract). This facilitates ensuring that the stent 100 does not remain rigid enough to prevent the scaring from contracting, given that such contraction of the scar can be beneficial in taking mass effect and pressure away from adjacent structures like nerves and organs.

When introducing elements of the present invention or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

What is claimed is:

1. A stent for placement in a blood vessel with a wall having an aneurysm, the stent comprising:
   an endovascular graft having a first end, a second end, and a tubular body that is expandable and extends from the first end to the second end; and
   a coagulation apparatus attached to the tubular body of the endovascular graft between the first end and the second end, the coagulation apparatus having a frame and a coagulant attached to the frame, wherein the coagulant comprises fibrous material that defines a porous web within the coagulation apparatus by which the frame is circumferentially tethered to the tubular body; wherein the fibrous material is arranged in a plurality of overlapping tiers, each tier of the plurality of overlapping tiers comprising at least one fibrous strand oriented to define a network of pores within the porous web, wherein each tier of the plurality of overlapping tiers circumscribes the tubular body; and wherein the porous web spans a space defined between the frame and the tubular body; and wherein, when the stent is deployed within the blood vessel, the tubular body extends across the aneurysm and is configured to expand at the first end and the second end to seal against the wall of the blood vessel such that blood is channeled across the aneurysm through the tubular body such that a pocket of blood is defined external to the tubular body, and wherein the frame is configured to expand into the pocket to orient the coagulant within the pocket and promote coagulation of the blood within the pocket.

2. The stent in accordance with claim 1, wherein the tubular body comprises a cage and a cover attached to the cage, and wherein the cage is expandable to seal the tubular body against the wall of the blood vessel.

3. The stent in accordance with claim 2, wherein the cover is fabricated from a substantially liquid-impermeable material.

4. The stent in accordance with claim 1, wherein the fibrous material is coupled between the endovascular graft and the frame such that radial expansion of the frame relative to the endovascular graft is limited.

5. The stent in accordance with claim 1, wherein the fibrous material is fabricated from thrombogenic material.

6. The stent in accordance with claim 1, wherein the plurality of tiers are each spaced from each other along a length of the tubular body.

7. The stent in accordance with claim 1, wherein the frame is fabricated from a shape memory alloy material.

8. The stent in accordance with claim 1, wherein the coagulation apparatus is configured to deploy when an amount of force applied thereto is less than a predetermined threshold, and is configured to collapse when the amount of force applied thereto is greater than a predetermined threshold.

9. A method of inhibiting endoleaks in a blood vessel with a wall having an aneurysm, the method comprising:
inserting a stent within the blood vessel at a site of the aneurysm, wherein the stent includes an endovascular graft, having a first end, a second end, and a tubular body, and a coagulation apparatus attached to the tubular body of the endovascular graft between the first end and the second end, the coagulation apparatus having a frame and a coagulant attached to the frame, wherein the coagulant comprises fibrous material that defines a porous web within the coagulation apparatus by which the frame is circumferentially tethered to the tubular body; wherein the fibrous material is arranged in a plurality of overlapping tiers, each tier of the plurality of overlapping tiers comprising at least one fibrous strand oriented to define a network of pores within the porous web, wherein each tier of the plurality of overlapping tiers circumscribes the tubular body; and wherein the porous web spans a space defined between the frame and the tubular body; and deploying the coagulation apparatus from a compressed state such that the frame expands into a pocket of blood, defined by the aneurysm, to orient the coagulant within the pocket and promote coagulation of the blood within the pocket.

10. The method in accordance with claim 9, wherein inserting a stent comprises positioning the stent within the blood vessel such that the tubular body extends across the aneurysm, and wherein the tubular body is configured to expand at a first end and a second end thereof to seal against the wall of the blood vessel.

11. The method in accordance with claim 9, wherein deploying the coagulation apparatus comprises unsheathing the coagulation apparatus.

12. The method in accordance with claim 9, wherein deploying the coagulation apparatus is with a balloon-expandable platform.

13. A stent comprising:
an endovascular graft having a first end, a second end, and a tubular body that is expandable and extends from the first end to the second end; and
a coagulation apparatus attached to the tubular body of the endovascular graft between the first end and the second end, the coagulation apparatus having a frame and a coagulant attached to the frame, wherein the coagulant comprises fibrous material that defines a porous web within the coagulation apparatus by which the frame is circumferentially tethered to the tubular body; wherein the fibrous material is arranged in a plurality of overlapping tiers, each tier of the plurality of overlapping tiers comprising at least one fibrous strand oriented to define a network of pores within the porous web, wherein each tier of the plurality of overlapping tiers circumscribes the tubular body; and wherein the porous web spans a space defined between the frame and the tubular body.

14. The stent in accordance with claim 13, wherein the tubular body comprises a cage and a cover attached to the cage, and wherein the cage is expandable to seal the tubular body against a wall of a blood vessel.

15. The stent in accordance with claim 14, wherein the cover is fabricated from a substantially liquid-impermeable material.

16. The stent in accordance with claim 13, wherein the coagulation apparatus extends circumferentially about the tubular body.

17. The stent in accordance with claim 13, wherein the fibrous material is coupled between the endovascular graft and the frame such that radial expansion of the frame relative to the endovascular graft is limited.

18. The stent in accordance with claim 13, wherein the fibrous material is fabricated from thrombogenic material.

19. The stent in accordance with claim 13, wherein the plurality of tiers are each spaced from each other along a length of the tubular body.

* * * * *